(12) United States Patent
Santilli et al.

(10) Patent No.: US 7,963,964 B2
(45) Date of Patent: *Jun. 21, 2011

(54) SURGICAL CLAMP ASSEMBLY WITH ELECTRODES

(76) Inventors: Albert N. Santilli, Pepper Pike, OH (US); Amit Patel, Salt Lake City, UT (US)

( * ) Notice: Subject to any disclaimer, the term of this patent is extended or adjusted under 35 U.S.C. 154(b) by 1016 days.

This patent is subject to a terminal disclaimer.

(21) Appl. No.: 11/697,034

(22) Filed: Apr. 5, 2007

(65) Prior Publication Data

US 2007/0244477 A1 Oct. 18, 2007

Related U.S. Application Data

(60) Continuation-in-part of application No. 10/631,052, filed on Jul. 29, 2003, now Pat. No. 7,455,678, which is a division of application No. 09/781,000, filed on Feb. 9, 2001, now Pat. No. 6,610,074.

(60) Provisional application No. 60/181,435, filed on Feb. 10, 2000.

(51) Int. Cl.
*A61B 18/14* (2006.01)
(52) U.S. Cl. ............ 606/51; 606/52; 606/205
(58) Field of Classification Search .......... 606/45–52, 606/151, 157, 158, 205–208
See application file for complete search history.

(56) References Cited

U.S. PATENT DOCUMENTS

| | | | |
|---|---|---|---|
| 848,126 A | 3/1907 | Roosevelt | |
| 1,513,367 A | 10/1924 | Brix | |
| 3,277,895 A | 10/1966 | Johnson | |
| 4,041,952 A * | 8/1977 | Morrison et al. | 606/42 |
| 4,106,508 A | 8/1978 | Berlin | |
| 5,133,724 A | 7/1992 | Wilson, Jr. et al. | |
| 5,158,563 A | 10/1992 | Cosman | |
| 5,261,917 A | 11/1993 | Hasson et al. | |
| 5,304,183 A * | 4/1994 | Gourlay et al. | 606/142 |
| 5,447,515 A | 9/1995 | Robicsek | |
| 5,618,307 A * | 4/1997 | Donlon et al. | 606/205 |
| 5,843,100 A | 12/1998 | Meade | |
| 5,921,996 A * | 7/1999 | Sherman | 606/157 |
| 5,925,052 A | 7/1999 | Simmons | |

(Continued)

OTHER PUBLICATIONS

Somnus Medical Technologies, Inc., Principles of Radiofrequency Thermal Ablation, Internet Article, 1997.
Meyer-Haake Medical Innovations, Internet Article, 2003-2004.
Dekko Medical Devices, Positive Temperature Coefficient (PTC) Heating Technology, 2005.

(Continued)

*Primary Examiner* — Michael Peffley
(74) *Attorney, Agent, or Firm* — Wayne D. Porter, Jr.

(57) ABSTRACT

A surgical clamp assembly includes a clamp having movable jaws, each of which has a clamping surface for engaging a portion of a patient's body. An electrode forms a portion of the clamping surface of at least one of the jaws, the electrode being capable of heating, severing, or cauterizing the portion of the patient's body that is grasped by the clamp. If desired, the clamp assembly can be provided with a retainer that prevents the jaws from being opened accidentally. The clamp assembly also can include an actuator that can be detached from the clamp and removed from the operative site, leaving the locked clamp in place. In this type of assembly, when it is desired to remove the clamp, the actuator can be reattached to the clamp and used to disengage the toothed retainer, and thereafter can be used to spread the jaws in order to permit the clamp to be removed.

22 Claims, 7 Drawing Sheets

U.S. PATENT DOCUMENTS

| | | | |
|---|---|---|---|
| 6,146,392 A | 11/2000 | Smith | |
| 6,235,027 B1 * | 5/2001 | Herzon | 606/51 |
| 6,511,480 B1 * | 1/2003 | Tetzlaff et al. | 606/51 |
| 6,610,074 B2 | 8/2003 | Santilli | |
| 6,758,846 B2 * | 7/2004 | Goble et al. | 606/41 |
| 2002/0120316 A1 * | 8/2002 | Hooven et al. | 607/101 |

OTHER PUBLICATIONS

Valleylab, Internet Advertisement and Information for LIGASURE Vessel Scaling System, Bipolar Electrosurgery, Coated Electrodes and Electrosurgical Forceps, 2005.

A.D.A.M., Inc., Electrocauterization, Internet Article, 2005.

* cited by examiner

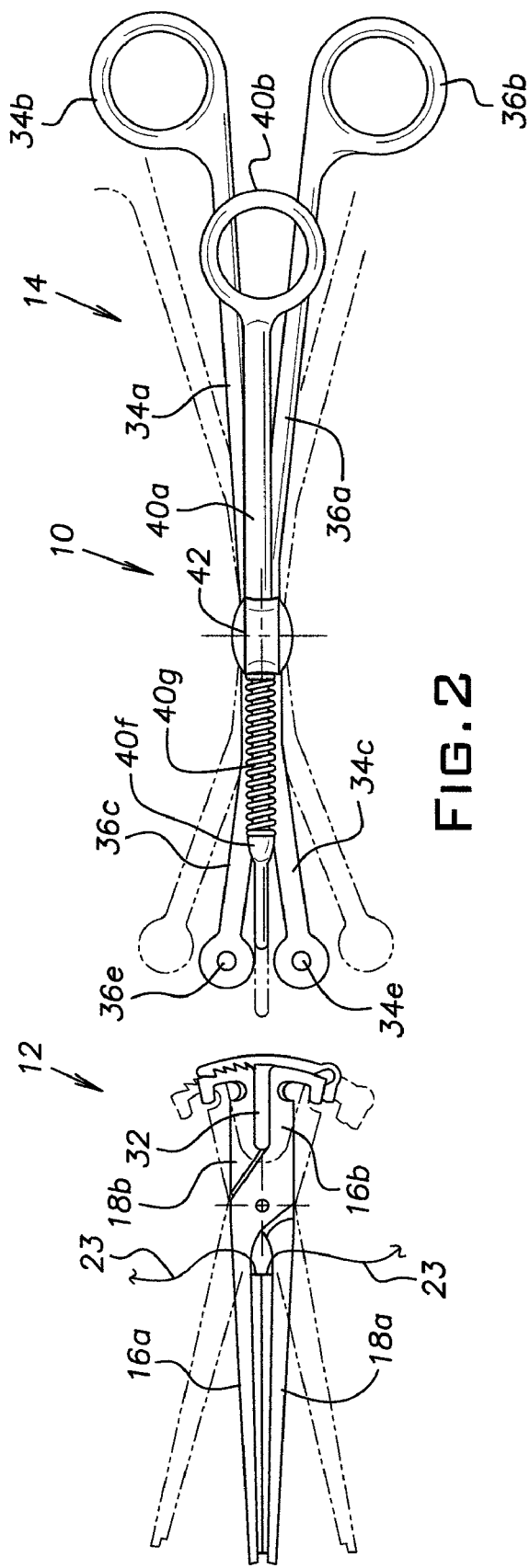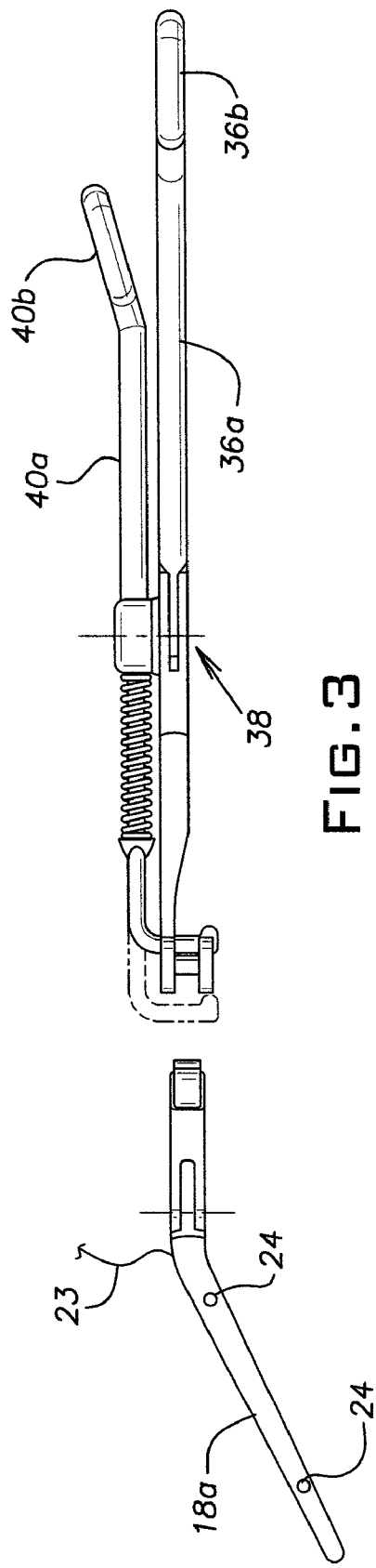
FIG. 2
FIG. 3

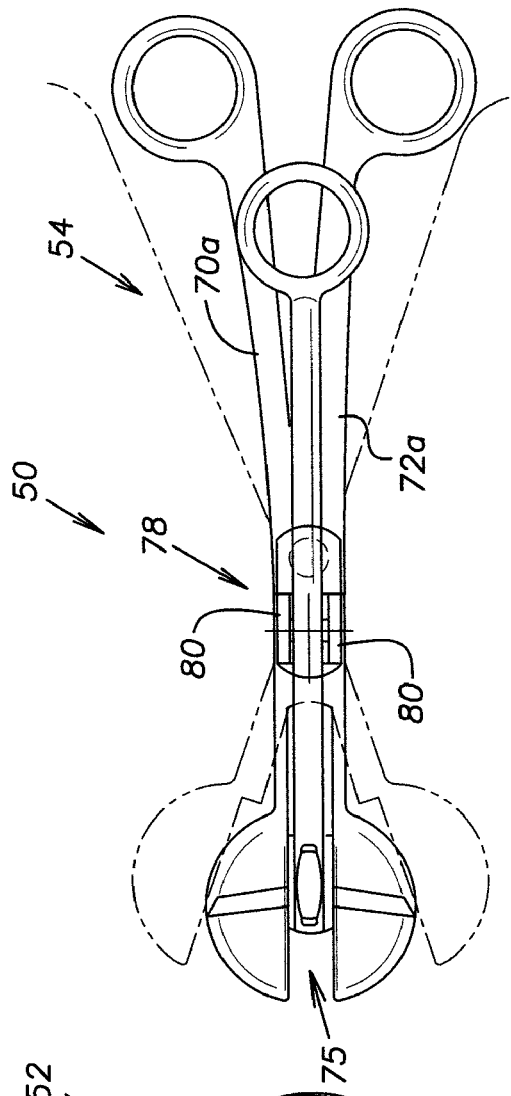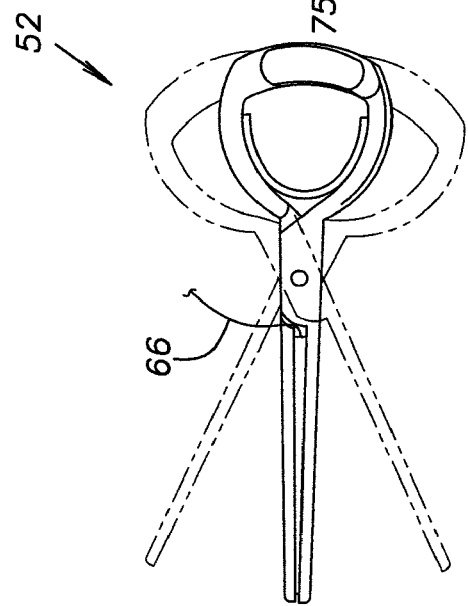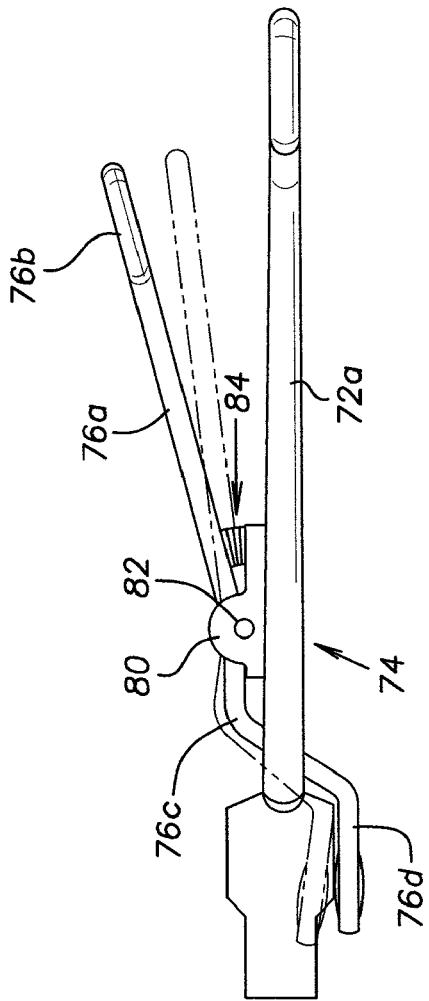

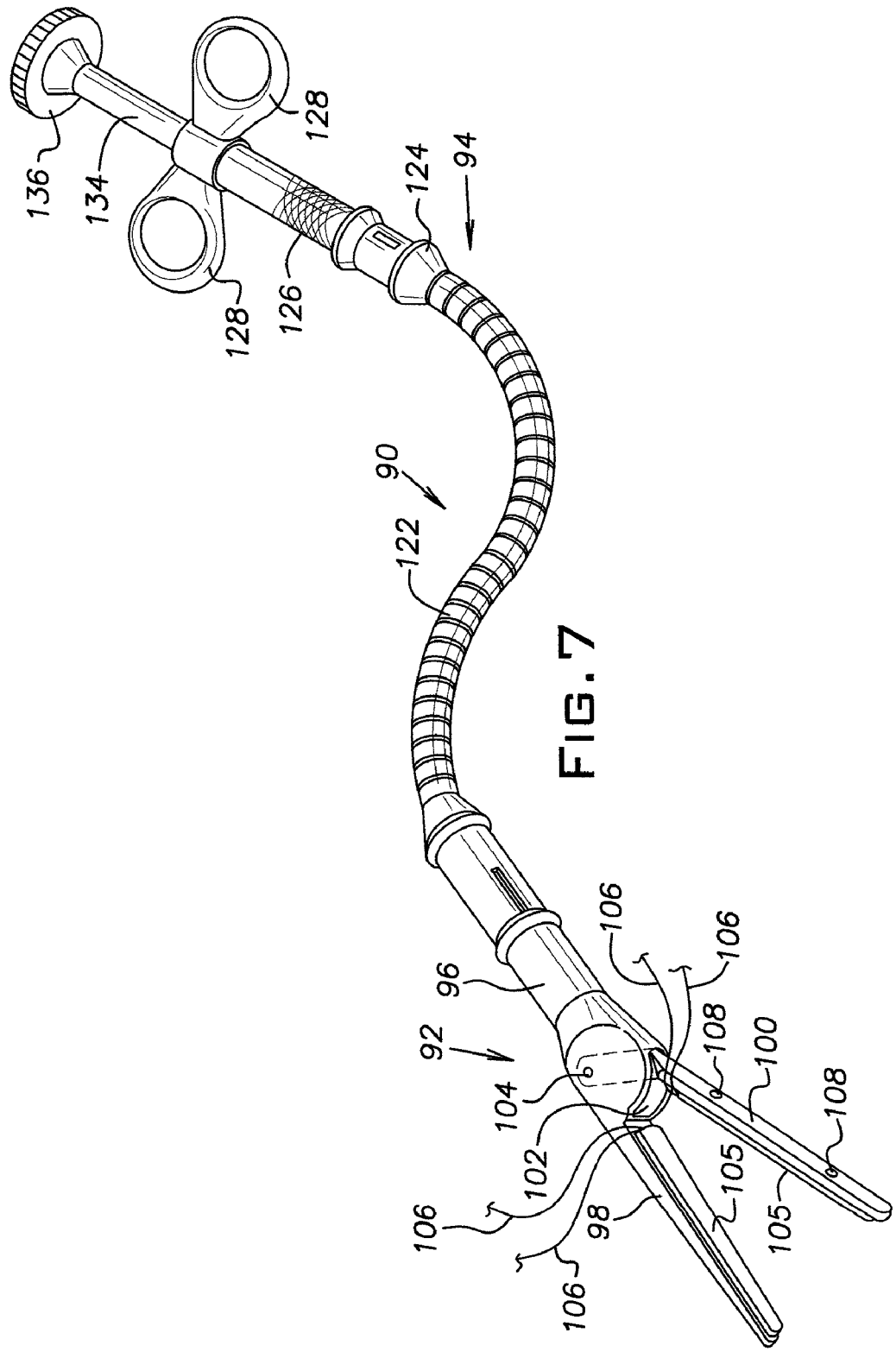

_US 7,963,964 B2_

SURGICAL CLAMP ASSEMBLY WITH ELECTRODES

REFERENCE TO PENDING APPLICATION

The present application is a continuation-in-part of application Ser. No. 10/631,052, filed Jul. 29, 2003, now U.S. Pat. No. 7,455,678, which is a division of application Ser. No. 09/781,000, filed Feb. 9, 2001, now U.S. Pat. No. 6,610,074, which claimed priority from provisional application Ser. No. 60/181,435, filed Feb. 10, 2000 by Albert N. Santilli.

BACKGROUND OF THE INVENTION

1. Field of the Invention

The invention relates to clamps for surgical procedures and, more specifically, to a clamp assembly having the capability to heat tissue that is engaged by the clamp assembly.

2. Description of the Prior Art

The invention will be discussed in the context of cardiac surgery, although it is to be understood that the invention has applicability to a wide range of surgical procedures. During the course of cardiac surgery in which cardiac function is arrested, it is necessary to isolate the heart and coronary blood vessels from the remainder of the circulatory system. Circulatory isolation of the heart and coronary blood vessels is usually accomplished by placing a mechanical cross clamp externally on the ascending aorta downstream of the ostia of the coronary arteries, but upstream of the brachiocephalic artery so that oxygenated blood from the cardiopulmonary bypass system reaches the arms, neck, head, and remainder of the body. Using conventional techniques, the sternum is cut longitudinally (a median sternotomy) thereby providing access between opposing halves of the anterior portion of the rib cage to the heart and other thoracic vessels and organs. Alternatively, a lateral thoracotomy is formed, wherein a large incision is made between two ribs and the ribs are retracted. A portion of one or more ribs may be permanently removed to optimize access.

Regardless of whether a sternotomy or a thoracotomy is performed (both collectively referred to herein as a "gross thoracotomy"), the opening in the chest wall must be large enough to permit a cross clamp to be placed externally on the ascending aorta, thereby isolating the heart and coronary arteries from the remainder of the arterial system. A problem with existing cross clamps is their excessive size. A cross clamp usually includes a clamping portion from which integral actuating handles project. The clamp occupies a relatively large portion of the operative site, thereby requiring that the sternum or ribs be retracted to a greater extent than is desired. This is a significant factor in open-chest surgery, because the trauma caused by creating large openings in the chest wall often entails weeks of hospitalization and months of recuperation time.

Recently, techniques have been developed to facilitate the performance of cardiac procedures such as heart valve repair and replacement, coronary artery bypass grafting, and the like, using minimally invasive techniques that eliminate the need for a gross thoracotomy. Coronary artery bypass grafting, heart valve repair and replacement, and other procedures can be performed through small incisions or cannulae positioned in the chest wall. In one recently developed technique, a clamp is introduced into the patient's thoracic cavity through a percutaneous intercostal penetration in the patient's chest, typically using a trocar sleeve. The clamp is detachably mounted to the distal end of a clamp positioner. After the clamp is positioned around the ascending aorta, the clamp is actuated from outside the patient's thoracic cavity to squeeze the aorta and partially or completely block fluid flow therethrough. The clamp then is disengaged from the distal end of the clamp positioner and the clamp positioner is removed from the thoracic cavity to provide enhanced access to the region in question.

Although the referenced device permits cardiac surgery to be conducted with significantly smaller openings formed in the chest wall, there is a concern about the reliability of the clamp and whether a connection can be reestablished between the clamp and the clamp positioner when it is necessary to remove the clamp. A failure of the clamp or the inability to remove the clamp could have disastrous consequences for the patient. An additional concern is that the referenced device employs a clamp made of metal that has no capability to heat tissue with which it comes in contact.

Despite the advantages of minimally invasive cardiac surgery, certain situations still call for the use of a gross thoracotomy. In such circumstances, there remains a need for an aorta cross clamp that is smaller than existing cross clamps but which is extremely reliable and easy to use. In those cases where minimally invasive surgery is indicated, there is a need for an aorta cross clamp that is easy to apply to the ascending aorta, which is reliable in use, and which can be removed without fail. There also is a need for a clamp that has the capability to heat tissue.

SUMMARY OF THE INVENTION

In response to the foregoing concerns, the present invention provides a new and improved surgical clamp assembly for grasping and heating portions of a patient's body. The invention includes a clamp having first and second jaws that are movable toward and away from each other, each jaw having a clamping surface that is intended to contact a desired portion of a patient's body. One or both clamping surfaces can be in the form of, or can include, one or more electrodes. The electrode or electrodes can be energized electrically so as to raise the temperature of the contacted tissue to a desired level. Through the use of suitable electrodes, the clamp can be used to heat, sever, or cauterize tissue.

The invention can be used with any type of clamp, including conventional scissors-type clamps. The invention also is effective when used with clamps having a removable actuator wherein the clamp is left in or on the patient's body in a locked position while the actuator is removed from the operative site. In one embodiment, a clamp having movable jaws is provided with a removable actuator having movable handles. Initially, the actuator is connected to the clamp with the jaws in an open position. When the actuator handles are closed, the jaws also will be closed. The clamp is provided with a toothed retainer that prevents the jaws from being opened accidently. The actuator can be detached from the clamp and removed from the operative site, leaving the locked clamp in place. When it is desired to remove the clamp, the actuator can be reattached to the clamp and used to disengage the toothed retainer. The actuator then can be used to spread the jaws in order to permit the clamp to be removed.

The clamp and the actuator are provided in two forms. In one form, the toothed retainer is engaged and disengaged by movement toward and away from the jaws ("horizontal" movement). In the other form, the toothed retainer is engaged and disengaged by movement generally perpendicular to the jaws ("vertical" movement).

In another embodiment, a clamp having movable jaws is provided with a slender, flexible, actuator that is not intended to be removed during use. The actuator has a proximal end that defines a handle and a distal end that is connected to the clamp. The jaws are actuated by axial movement of a screw that is connected to the end of a cable included as part of the actuator. The screw passes through a slotted nut that permits non-rotational axial movement of the screw in one direction, but which requires that the screw be rotated in order to move in the opposite direction. A stem having a knob is attached to the proximal end of the cable and extends outwardly from the handle.

When the knob is pushed inwardly (toward the handle), the stem and the cable are advanced, thereby axially moving the screw and closing the jaws of the clamp. The nut prevents the jaws from being opened inadvertently. When is it necessary to remove the clamp, the knob is rotated. This causes the stem, cable, and screw to be rotated. When the screw is rotated, it is moved axially relative to the nut and pulls the jaws to the open position.

The present invention provides a surgical clamp that can be used for a variety of surgical procedures, including cardiac surgery during either a gross thoracotomy or a minimally invasive procedure such as a percutaneous intercostal penetration. The ability to heat, sever, or cauterize the tissue contacted by the clamp provides the surgeon with the capability to deal with a wide range of surgical situations that may be encountered. With any embodiment of the invention, the clamp assembly is compact, reliable, and easy to apply and remove. The foregoing and other features and advantages of the invention will be apparent from an examination of the specification and claims that follow, including the accompanying drawings.

BRIEF DESCRIPTION OF THE DRAWINGS

FIG. 2. is a top plan view of the clamp assembly of FIG. 1;

FIG. 3. is a side elevational view of the clamp assembly of FIG. 1;

FIG. 5 is a top plan view of the clamp assembly of FIG. 4;

FIG. 6 is a side elevational view of the clamp assembly of FIG. 4;

FIG. 7 is a perspective view of a surgical clamp assembly according to the invention in which a clamp having electrodes is mounted at the end of a flexible actuator;

DESCRIPTION OF THE PREFERRED EMBODIMENT

The invention can be used with any type of clamp, including conventional scissors-type clamps. The invention also is effective when used with clamps having a removable actuator wherein the clamp is left in or on the patient's body in a locked position while the actuator is removed from the operative site. The invention will be described in conjunction with clamps having a removable actuator.

Figure 1:
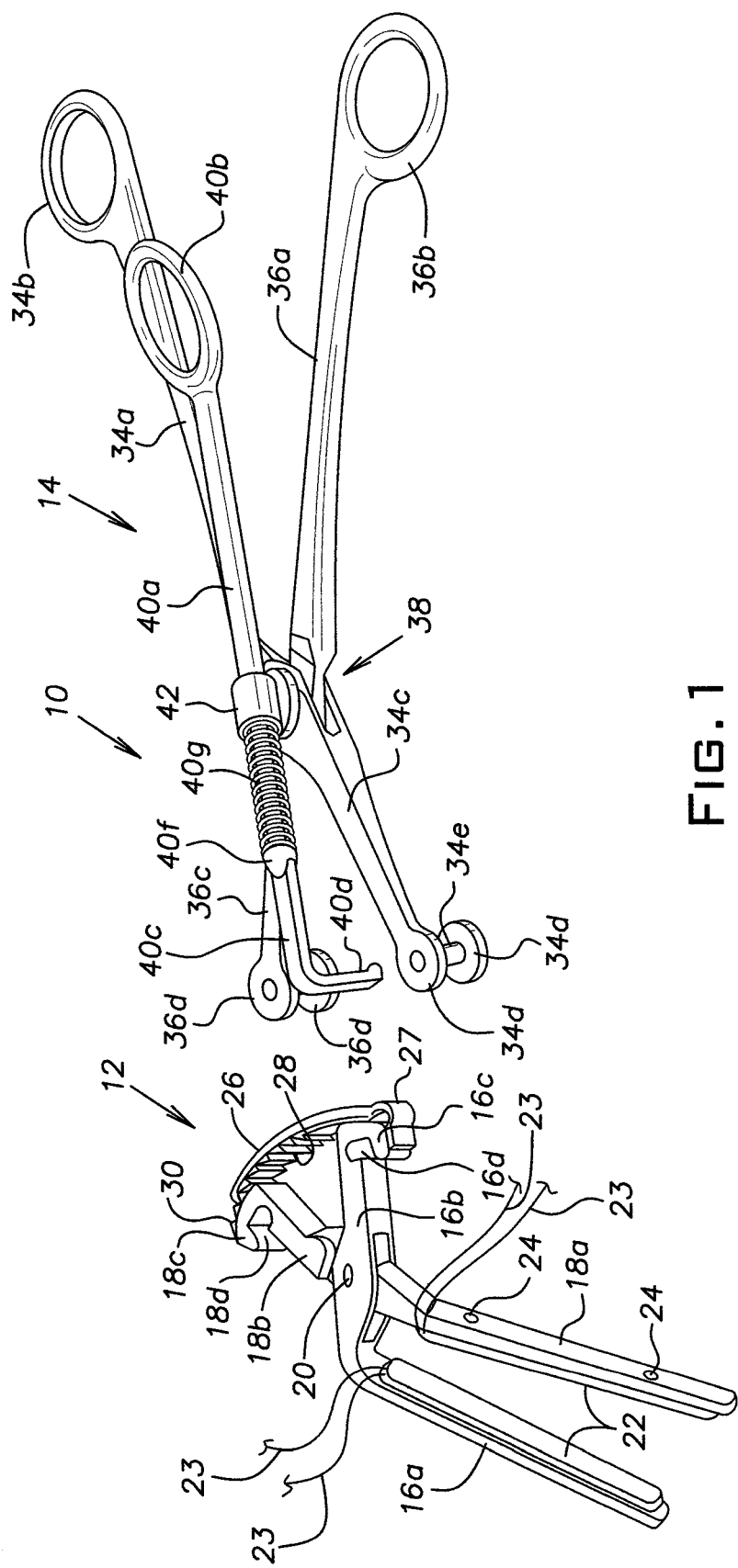
FIG. 1 is a perspective view of a surgical clamp assembly according to the invention in which a clamp having electrodes is disposed adjacent an actuator.

Referring to FIGS. 1-3, a surgical clamp assembly according to the invention is indicated by the reference numeral 10. The clamp assembly 10 is especially adapted for use during a gross thoracotomy, although it can be used for numerous other surgical procedures, if desired. The clamp assembly 10 includes a clamp 12 and an actuator 14. The clamp 12 has a first jaw 16a and a second jaw 18a. A handle 16b having spaced sides is connected to the jaw 16a. The handle 16b includes a formation 16c at its end. The formation 16c has a slotted opening 16d. The second jaw 18a is similar to the jaw 16a. A handle 18b is connected to the jaw 18a and includes a formation 18c at its end. A slotted opening 18d is provided for the formation 18c.

The handle 16b is defined by a pair of spaced sides through which the handle 18b extends. The handles 16b, 18b are joined for pivotal movement by a hinge pin 20. Each of the jaws 16a, 18a is provided with a plurality of electrodes 22 that form a part of a clamping surface intended to engage a portion of a patient's body. A pair of wires 23 extend from the electrodes 22 for connection to a source of electrical power (not shown). The electrodes 22 are attached to the respective jaws 16a, 18a by fasteners 24. The longitudinal axes of the jaws 16a, 18a and the handles 16b, 18b are disposed relative to each other at an angle within the range of about 25-30 degrees, preferably about 27 degrees, when viewed from the side (FIG. 3).

A curved ratchet bar 26 is connected to the formation 16c by means of a spring mounting 27. The ratchet bar 26 lies in the arc of a circle whose radius is approximately equal to the distance from the hinge pin 20 to the ends of the handles 16b, 18b. The mounting 27 biases the ratchet bar 26 toward the formations 16c, 18c. A plurality of teeth 28 are provided on that portion of the ratchet bar 26 which faces the formations 16c, 18c. A plurality of teeth 30 are provided on the formation 18c and face the teeth 28. The teeth 28, 30 are oriented such that they engage each other when the handles 16b, 18b are attempted to be moved apart, thereby preventing the handles 16b, 18b from being opened. In effect, the handle 18b and the teeth 30 form a pawl that permits closing movement of the jaws 16a, 18a, but which prevents opening movement of the jaws 16a, 18a. When the handles 16b, 18b (and hence, the jaws 16a, 18a) are closed, a small gap 32 (FIG. 2) is formed between the handles 16b, 18b.

The actuator 14 includes first and second handles 34a, 36a having finger loops 34b, 36b at the proximal ends thereof. Arms 34c, 36c are connected to and project from the handles 34a, 36a. A pair of spaced discs 34d, 36d are disposed at the ends of the arms 34c, 36c. The discs 34d, 36d are spaced apart a distance slightly greater than the width of the formations 16c, 18c. The discs 34d, 36d are joined by pins 34e, 36e. The pins 34e, 36e have a diameter slightly less than that of the slotted openings 16d, 18d.

The handles 34a, 36a are joined for pivotal movement by a hinge pin indicated generally by the reference numeral 38. The actuator 14 includes a third handle 40a. The handle 40a has a finger loop 40b at the proximal end thereof. The finger loop 40b lies in a plane inclined upwardly at an angle within the range of about 15-20 degrees, preferably about 17 degrees, from the plane in which the handle 40a lies. An arm 40c is connected to and projects from the handle 40a. A finger 40d extends from the arm 40c at a right angle to the longitudinal axis of the arm 40c. The diameter of the finger 40d is slightly less that the width of the space 32.

A sleeve 42 is disposed atop the hinge pin 38. The handle 40a extends through the sleeve 42. An enlarged stop 40f is mounted on the arm 40c. A spring 40g is fitted over the arm 40c and engages the sleeve 42 and the stop 40f. The spring 40g biases the finger 40d away from the sleeve 42 (to the left as viewed in FIGS. 1-3).

Operation of the Clamp Assembly 10

When it is desired to use the clamp 12 to compress a portion of a patient's body, the handles 34a, 36a are moved apart (to the dashed line position shown in FIG. 2) so that the pins 34e, 36e can be engaged with the slotted openings 16d, 18d, respectively. The finger 40d will be disposed in that space defined by the handles 16b, 18b, and the ratchet bar 26. When the finger loops 34b, 36b are moved toward each other (to the solid line position shown in FIG. 2), the handles 16b, 18b will be moved toward each other, thereby closing the jaws 16a, 18a. The jaws 16a, 18a will remain closed due to the interaction of the teeth 28, 30. The actuator 14 can be removed from the now-closed clamp 12 by moving the finger loops 34b, 36b slightly apart and thereafter pushing the actuator 14 slightly toward the clamp 12. The actuator 14 then can be moved clear of the clamp 12 by spreading the finger loops 34b, 36b apart.

When it is desired to remove the clamp 12, the foregoing procedure is reversed so that the actuator 14 is reattached to the clamp 12. If the surgeon's thumb and middle finger have been used to manipulate the actuator 14, the surgeon can then place the index finger in the finger loop 40b and pull the finger loop 40b to the right as viewed in FIGS. 1-3, against the bias exerted by the spring 40g. The finger 40d will engage the ratchet bar 26, causing the teeth 28, 30 to be disengaged. Thereafter, the finger loops 34b, 34c can be spread apart in order to open the jaws 16a, 18a. The clamp assembly 10 then can then be removed from the operative site.

A Second Embodiment

Figure 4:
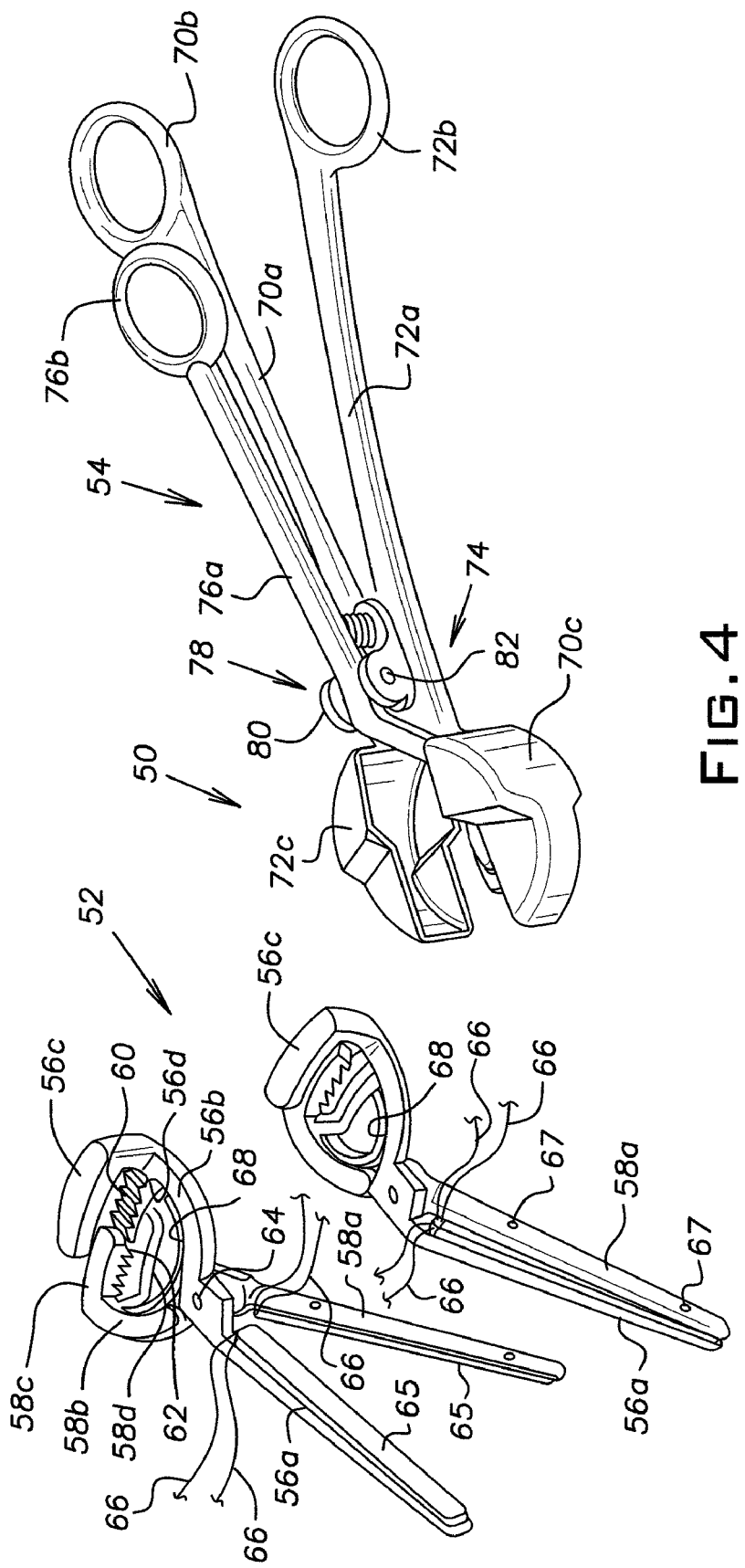
FIG. 4 is a view similar to FIG. 1 showing an alternative surgical clamp assembly according to the invention.

Referring now to FIGS. 4-6, an alternative surgical clamp assembly is indicated by the reference numeral 50. The assembly 50 is especially adapted for use during a gross thoracotomy, although it can be used for numerous other surgical procedures, if desired The clamp assembly 50 includes a clamp 52 and an actuator 54. The clamp 52 has a first jaw 56a and a second jaw 58a. A curved handle 56b is connected to the first jaw 56a. The handle 56b includes an upper, curved bar 56c at its end and a lower, curved bar 56d that is parallel to, but spaced from, the upper bar 56c. The second jaw 58a is similar to the arm 56a. A handle 58b is connected to the jaw 58a and includes an upper, curved bar 58c at its end and a lower, curved bar 58d that is parallel to, but spaced from, the upper bar 58c.

A plurality of teeth 60 are provided on the lower bar 56d, while a plurality of teeth 62 are provided on the upper bar 58c. The bars 56c, 58d do not have any teeth. As can be seen in FIG. 4, the bars 56c, 56d, 58c, 58d are fitted together so that the teeth 60, 62 engage each other when the handles 56b, 58b are attempted to be moved apart, thereby preventing the handles 56b, 58b from being opened. In turn, the jaws 56a, 58a will be prevented from opening. The upper bar 56c is spaced at a small distance from the bar 58c, while the lower bar 56d is spaced a small distance from the bar 58d.

The handles 56b, 58b are joined for pivotal movement by a hinge pin 64. Each of the jaws 56a, 58a is provided with a plurality of electrodes 65 that form a part of a clamping surface intended to engage a portion of a patient's body. A pair of wires 66 extend from the electrodes 65 for connection to a source of electrical power (not shown). The electrodes 65 are attached to the respective jaws 56a, 58a by fasteners 67. A curved spring 68 is disposed between the handles 56b, 58b and causes the handles 56b, 58b to be biased apart. The longitudinal axes of the jaws 56a, 58a and the handles 56b, 58b are disposed relative to each other at an angle within the range of about 25-30 degrees, preferably about 27 degrees, when viewed from the side (FIG. 6). When viewed from above (FIG. 5), the bars 56c, 56d, 58c, 58d lie in the arc of a circle whose radius is approximately equal to the distance from the hinge pin 64 to the ends of the handles 56b, 58b.

The actuator 54 includes first and second handles 70a, 72a having finger loops 70b, 72b at the proximal ends thereof. A pair of opposed shells 70c, 72c are connected to the handles 70a, 72a, respectively. The shells 70c, 72c are of a size and shape to receive the curved handles 56b, 58b, including the upper and lower curved bars 56c, 58c, 56c, 58d. The handles 70a, 72a are joined for pivotal movement by a hinge pin indicated generally by the reference numeral 74. When the handles 70a, 72a (and, hence, the shells 70c, 72c) are closed, a small gap 75 (FIG. 5) is formed between the shells 70c, 72c.

The actuator 54 includes a third handle 76a having a finger loop 76b at the proximal end thereof. The handle 76a has a generally ogee-shaped distal end 76c that includes an axially extending lower portion 76d. The lower portion 76d is adapted to fit into the gap 75 between the closed shells 70c, 72c and engage the lower curved bar 58d.

The actuator 54 includes a formation 78 which is connected to the hinge 74. A pair of spaced tabs 80 are included as part of the formation 78. A hinge pin 82 extends through the tabs 80 and the handle 76a. A spring 84 is disposed intermediate the upper surface of the formation 78 and the underside of the handle 76a. The spring 84 biases the handle 76a away from the first and second handles 70a, 72a to that position shown by the solid lines in FIG. 6.

Operation of the Clamp Assembly 50

When it desired to use the clamp 52 to compress a portion of a patient's body, the shells 70c, 72c are disposed about the ends of the curved handles 56b, 58b in the open position. As the handles 70a, 72a are moved toward each other, the jaws 56a, 58a will be moved to the solid line position in FIG. 5. After the handles 70a, 72a have been moved apart and the shells 70c, 72c have been removed from the handles 56b, 58b, the clamp 52 will remain in the closed position shown by the solid lines in FIG. 5 due to the engagement between the opposed teeth 60, 62.

When it is desired to remove the clamp 52, the foregoing procedure is reversed and the handle 76a is pressed towards the handles 70a, 72a. The lower portion 76d will be pivoted into contact with the lower curved bar 58d. Continued movement of the handle 76a will cause the upper curved bar 56d to engage the underside of the upper walls that define the shells 70c, 72c. Thereafter, continued movement of the handle 76a will cause the bars 58c, 56d to be moved relative to each other such that the teeth 60, 62 become disengaged. Under the influence of the spring 68, the handles 56b, 58b (and, hence, the jaws 56a, 58a) will be moved apart as the handles 70a, 72a are moved apart from each other. After the jaws 56a, 58a have been moved enough to release their grip on the aorta, the clamp 52 and the actuator 54 can be retracted from the operative site.

A Third Embodiment

Figure 8:
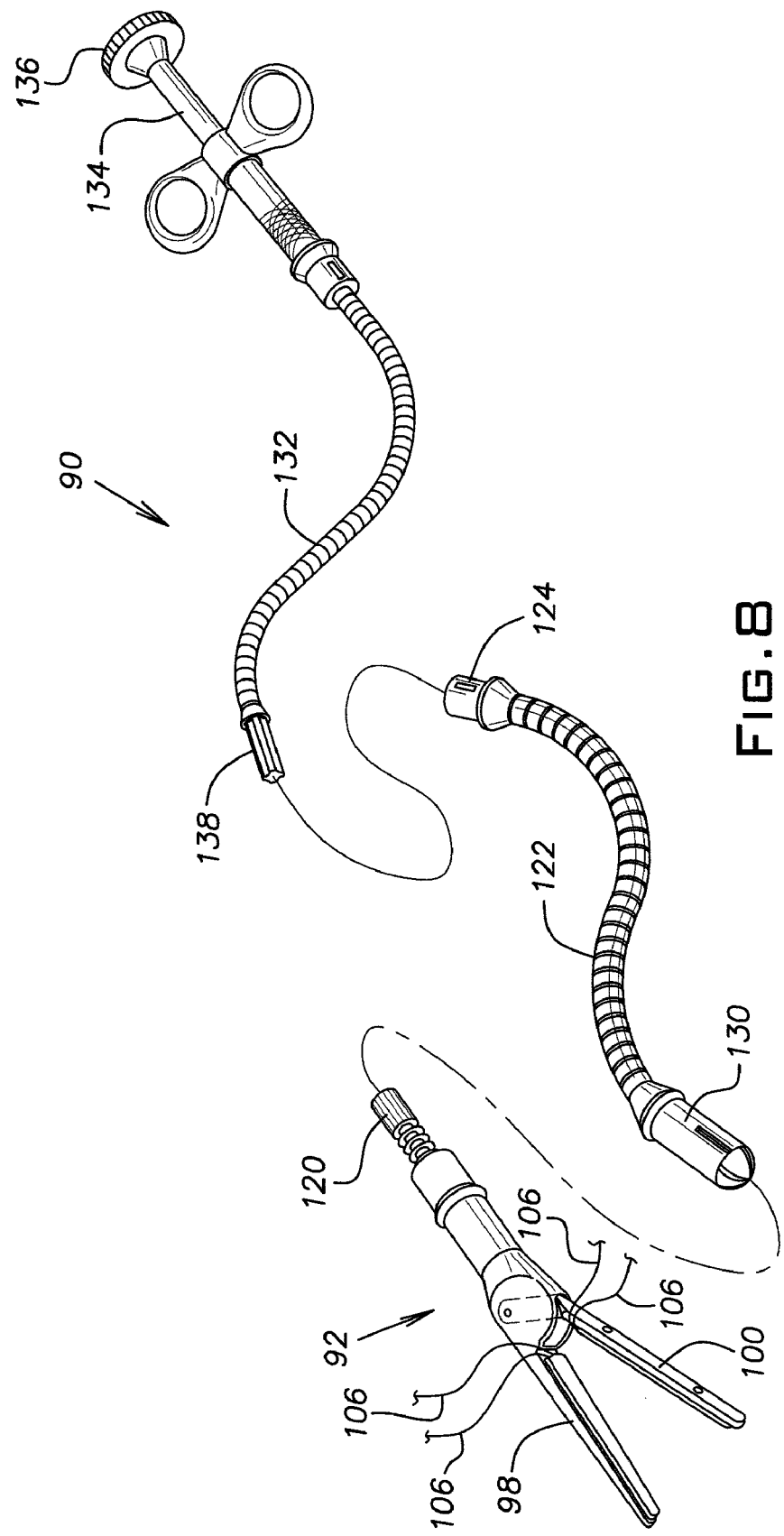
FIG. 8 is a view similar to FIG. 7 in which the components of the clamp assembly have been separated and spaced apart for purposes of clarity of illustration.
Figure 9:
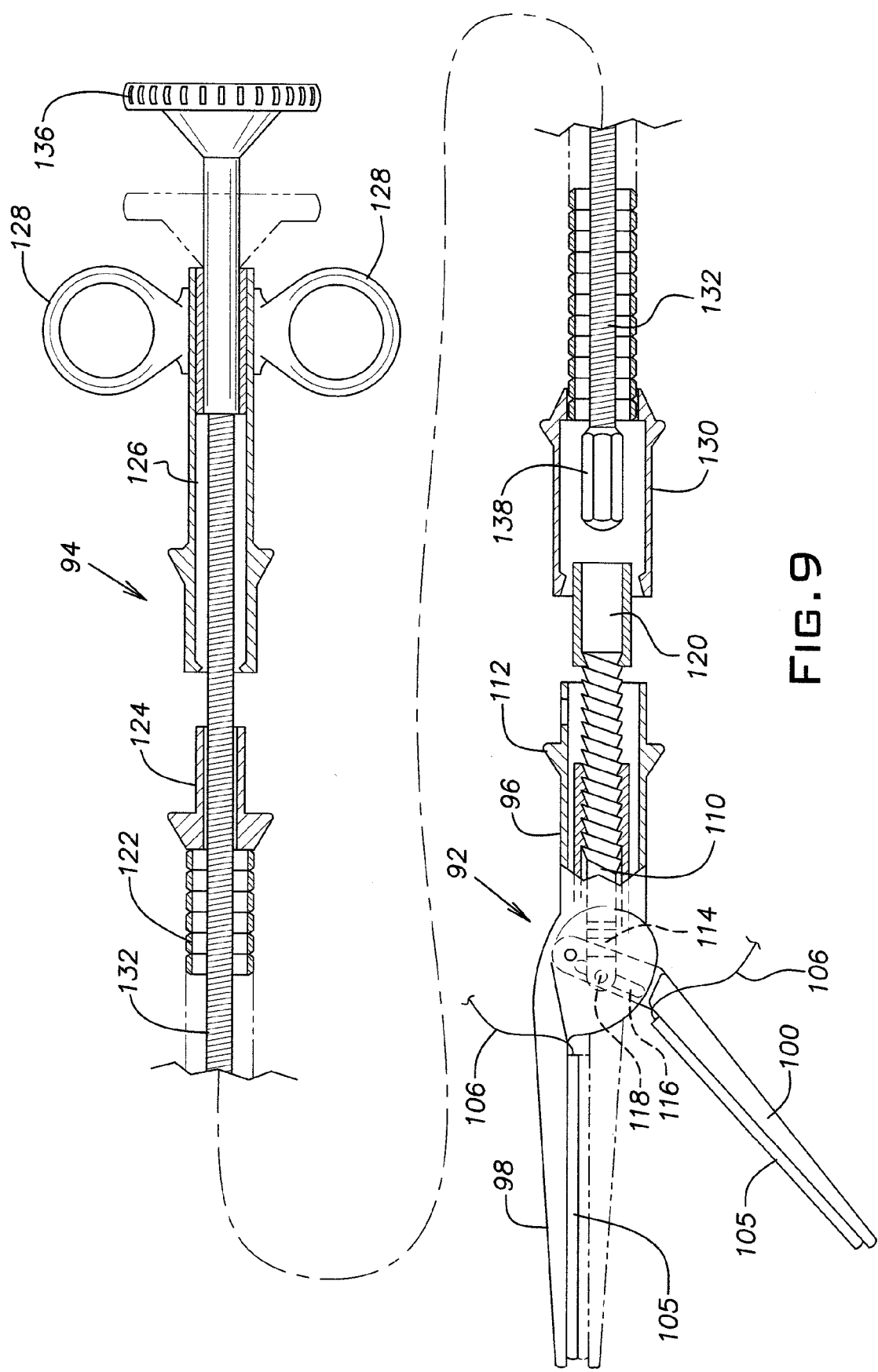
FIG. 9 is a enlarged plan view, partly in cross-section, of the proximal and distal ends of the actuator of FIG. 7.

Referring now to FIGS. 7-9, another surgical clamp assembly is indicated by the reference numeral 90. The assembly 90 is especially adapted for use during minimally invasive cardiac surgery, although it can be used for numerous other surgical procedures, if desired. The assembly 90 includes a clamp 92 and an actuator 94. The clamp 92 has a cylindrical base 96 with a bore therethrough. A first jaw 98 is rigidly connected to the cylindrical base. A second jaw 100 is pivotally connected to the cylindrical base 96. The connection is established by a slot 102 formed in the first jaw 98. A hinge pin 104 extends through the jaws 98, 100. Each of the jaws 98, 100 is provided with a plurality of electrodes 105 that form a part of a clamping surface intended to engage a portion of a patient's body. A pair of wires 106 extend from the electrodes 105 for connection to a source of electrical power (not shown). The electrodes 105 are attached to the respective jaws 98, 100 by fasteners 108.

A screw 110 is disposed within the bore. A screw 110 is a so-called quick advance screw having coarse, tapered threads. A slotted nut 112 is connected to the cylindrical base 96 at that end opposite the jaws 98, 100. A link 114 is connected to the jaw 100. The connection is established by a slot 116 formed in the jaw 100 and a pin 118 that is connected to the link 116 which extends through the slot 116. The link 114 is rotatably connected to the screw 110. A drive connector 120 having a plurality of longitudinally extending keyways is connected to the other end of screw 110.

The actuator 94 includes a flexible housing 122. A fitting 124 is connected to the proximal end of the housing 122. A cylindrical, hollow handle 126 is connected to the fitting 124. A pair of finger loops 128 extend from opposite sides of handle 126. A fitting 130 is connected to the distal end of the housing 122. The fitting 124 is releasably connected to the handle 126, while the fitting 130 is releasably connected to the cylindrical base 96. Although the fittings 124, 130 can be disconnected for purposes of cleaning and sterilization, it is expected that they will remain connected as shown in FIG. 7 during the course of a surgical procedure.

An elongate flexible cable 132 extends through the housing 122. A cylindrical stem 134 is connected to the proximal end of the cable 132. A knurled knob 136 is disposed at the end of the stem 134. A splined drive member 138 is connected to the distal end of the cable 132. The splines on the drive member 138 engage the keyways in the drive connector 120 so as to establish a driving connection. As will be apparent from an examination of FIG. 9, the drive member 138 and the connector 120 can be moved axially relative to each other.

Operation of the Clamp Assembly 90

Starting from the position shown FIG. 7, the clamp 92 can be actuated to cause the jaws 98, 100 to clamp a portion of a patient's body by pushing the stem 134 toward the handle 126 (from the full line position in FIG. 9 to the dashed line position in FIG. 9). When the handle 126 is moved in this manner, the cable 132 is moved within the housing so that axial force is applied to the connector 120 and, hence, to the screw 110. Due to the orientation of the screw threads relative to the nut 112, the screw 110 will be moved axially, thereby causing the jaw 100 to be pivoted toward the jaw 98. Although the screw 110 can be advanced toward a jaw-closed position without rotation, it cannot be retracted without rotation for two reasons: (1) if the cable 132 is pulled out of the housing 122, the drive member 138 will be disconnected from the drive connector 120, as shown in FIG. 9, and (2) the nut 112 will engage the threads of the screw 110 so as to prevent retraction of the screw 110.

When it is desired to loosen the jaws 98, 100 in order to remove the clamp 92 from the clamped portion of the patient's body, it is necessary to rotate the knob 136 so that the stem 134, cable 132, drive member 138, connector 120, and screw 110 all are rotated. When the screw 110 is rotated relative to the nut 112, the screw 110 will be retracted from the bore in the base 96, thereby causing the jaw 100 to be pulled toward a jaw-open position. After sufficient movement of the jaw 100 has occurred, the clamp 92 can be removed from the operative site.

The electrodes 22, 65, 105 can be any type of heating element capable of heating body tissues to a desired temperature. Such electrodes can operate by resistance heating, radio frequency heating, ultrasonic heating, or any other technique that can be used to heat electrodes or tissue that is in contact with the electrodes 22, 65, 105. It is possible to use the electrodes 22, 65, 105 to cauterize tissue, sever tissue, or merely heat tissue to an above-body temperature for therapeutic purposes.

Electrodes that are suitable for surgical purposes and which operate on different principles are commercially available from a number of sources. One such type of suitable electrode is a monopolar or bipolar electrode that is used for electro-surgery and which is available from Valleylab, 5920 Longbow Drive, Boulder, Colo. 80301. Ceramic heating elements made from barium titanate are believed to be capable of being used for surgical or therapeutic purposes and are available from Dekko Medical Devices, Kendaliville, Ind. 46755. Other suitable types of electrodes are commercially available.

It is possible for the various components of the invention to be modified and still produce a satisfactory product. For example, and without limitation as to the type of changes that are within the scope of the invention, the embodiment of FIGS. 1-3 could be provided as a third class lever similar to the embodiment of FIGS. 7-9, that is, the handles 16b, 18b could be eliminated and the ratchet bar 26 and the formations 16c, 18c could be positioned between the hinge pin 20 and the electrodes 22. In this case, the ratchet bar 26 would be on the top or bottom of the jaws 16a, 18a or it would extend through an opening formed in one of the jaws 16a, 18a. The embodiments of FIGS. 4-6 could be reconfigured similarly. The embodiment of FIGS. 7-9 could be provided in the form of a first class lever by connecting a handle to the second jaw 100, in a manner similar to the embodiments of FIGS. 1-3 and 4-6.

Although the invention has been described in its preferred form with a certain degree of particularity, it will be understood that the present disclosure of the preferred embodiment has been made only by way of example, and that various changes may be resorted to without departing from the true spirit and scope of the invention as hereinafter claimed. It is intended that the patent shall cover, by suitable expression in the appended claims, whatever degree of patentable novelty exists in the invention disclosed.

What is claimed is:

1. A surgical clamp assembly for grasping and heating portions of a patient's body, comprising:
   a clamp having first and second jaws that are movable toward and away form each other, each jaw having a clamping surface that faces the other jaw and which engages a selected portion of a patient's body;
   a retainer operatively connected to the first and second jaws and movable between locked and unlocked positions, the retainer when in the locked position permitting the jaws to move toward each other but preventing the jaws from moving away from each other, and when in the unlocked position permitting the jaws to move away from each other;
   an actuator selectively and operatively engageable with and disengageable from the first and second jaws, the actuator enabling a user to open and close the jaws, wherein the actuator has first and second arms that are movable toward and away from each other, and further comprising a third arm selectively engageable with and disengageable from the retainer, the third arm being movable between a first position where the third arm is disposed adjacent the retainer when the retainer is in the locked position and a second position where the third arm engages the retainer and displaces it to the unlocked position; and an electrode forming a portion of the clamping surface of at least one of the jaws, the electrode capable of heating the portion of the patient's body that is grasped by the clamp to a desired temperature.

2. The surgical clamp assembly of claim 1, further comprising:
   a first handle to which the first jaw is connected;
   a second handle to which the second jaw is connected;
   a hinge pin that connects the handles for pivotal movement;
   each handle having an end remote from the hinge that is configured to define a slotted opening, the handles, when in the jaw-locked position, having a space therebetween;
   a ratchet bar included as part of the retainer, the ratchet bar being connected at one end to a selected one of the handles and including a plurality of teeth on a surface facing the handles;
   a plurality of teeth on the other of the handles, the teeth on the handle adapted to engage the teeth on the ratchet bar;
   the ratchet bar being curved to a radius from the hinge pin that approximates the radius of the ends of the handles from the hinge pin; and
   the ratchet bar being spring-mounted to the selected handle with a bias toward contact with the end of the handle.

3. The surgical clamp assembly of claim 2, wherein the actuator includes:
   a first arm connected to the first handle, the first handle having a finger loop;
   a second arm connected to the second handle, the second handle having a finger loop;
   the first and second handles being connected to each other by a hinge;
   a third arm connected to a third handle, the third handle having a finger loop, the third arm having a finger disposed at right angles to the third arm, the finger being engageable with the ratchet bar;
   a sleeve is connected to the hinge, the third arm extending through the sleeve;
   a stop is mounted on the third arm;
   a spring is disposed between the sleeve and the stop to bias the third arm to a finger-extended position; and
   the ends of the first and second arms include spaced-apart discs that are connected by a pin, the pin adapted to fit within one of the slotted openings.

4. The surgical clamp assembly of claim 1, further comprising:
   a first handle that is connected to the first jaw;
   a second handle that is connected to the second jaw;
   a hinge pin that connects the handles for pivotal movement;
   a spring that is disposed between the handles and biases the handles apart;
   a first ratchet bar included as part of the retainer that is connected at one end to a selected one of the handles, the first ratchet bar including a plurality of teeth;
   a second ratchet bar that is connected at one end to the other of the handles, the second ratchet bar including a plurality of teeth, the ratchet bars being disposed parallel to each other with the teeth on the respective ratchet bars facing each other and engaging each other;
   a first spacer bar disposed parallel to the first ratchet bar, the first spacer bar being connected to the end of the selected handle, the first spacer bar and the first ratchet bar being spaced apart a distance sufficient for the second ratchet bar to be received therebetween; and
   a second spacer bar disposed parallel to the second ratchet bar, the second spacer bar being connected to the end of the handle to which the second ratchet bar is connected, the second spacer bar and the second ratchet bar being spaced apart a distance sufficient for the first ratchet bar to be received therebetween.

5. The surgical clamp assembly of claim 4, further comprising:
   a first arm included as part of the actuator, the first arm being connected to the first handle;
   a finger loop included as part of the first handle;
   a second arm included as part of the actuator, the first arm being connected to the second handle;
   a finger loop included as part of the second handle;
   a hinge that connects the first and second handles to each other;
   a third arm connected to a third handle, the third handle having a finger loop, the third arm being ogee-shaped and having an axially extending lower portion, the axially extending lower portion being engageable with a selected one of the first or second spacer bars;
   a formation connected to the hinge, the formation having a pair of spaced tabs through which the third arm extends;
   a second hinge pin extending through the third arm and the tabs, the second hinge pin being disposed at right angles to the first hinge pin;
   a spring disposed between the formation and the third arm to bias the third arm to position where the axially extending position is disposed adjacent a selected one of the first or second spacer bars;
   shells included as part of the ends of the first and second arms, the shells adapted to receive the first and second handles of the clamp, the shells being movable toward each other upon movement of the first and second handles of the actuator so as to move the first and second handles of the clamp toward each other; and
   the shells defining a space therebetween when the shells are closed, the space being of a size and shape to permit the axially extending lower portion of the third arm to pass therebetween.

6. The surgical clamp assembly of claim 1, further comprising an electrode on both jaws.

7. The surgical clamp assembly of claim 1, wherein the electrode is removable from the jaw to which it is attached.

8. The surgical clamp assembly of claim 1, wherein the electrode operates by a technique selected from the group consisting of resistance heating, radio frequency heating, and ultrasonic heating.

9. The surgical clamp assembly of claim 1, wherein the electrode is monopolar or bipolar.

10. The surgical clamp assembly of claim 1, wherein the electrode has a ceramic heating element made of barium titanate.

11. The surgical clamp assembly of claim 1, wherein the electrode has a surface that is heated substantially uniformly.

12. The surgical clamp assembly of claim 1, wherein the electrode has a surface that is heated non-uniformly.

13. A surgical clamp assembly for grasping and heating portions of a patient's body, comprising:
   a clamp having first and second jaws that are movable toward and away form each other, each jaw having a clamping surface that faces the other jaw and which engages a selected portion of a patient's body;
   a retainer operatively connected to the first and second jaws and movable between locked and unlocked positions, the retainer when in the locked position permitting the jaws to move toward each other but preventing the jaws from moving away from each other, and when in the unlocked position permitting the jaws to move away from each other;

an actuator selectively and operatively engageable with and disengageable from the first and second jaws, the actuator enabling a user to open and close the jaws;

a flexible, elongate housing having first and second ends, the clamp being connected to the first end;

a fitting included as part of the second end of the housing to which the handle is secured, the handle having a pair of finger loops, and a stem having a knob;

an elongate actuator in the form of a cable disposed within the housing and operatively connected to the jaws such that axial movement of the actuator within the housing causes the jaws to move toward or way from each other;

the retainer being disposed within the housing, the retainer having two modes of operation, the retainer in the first mode permitting the actuator to move within the housing such that the jaws are moved toward each other but not away from each other, and the retainer in the second mode permitting the actuator to be moved within the housing such that the jaws are moved away from each other;

a handle connected to the second end of the housing;

the stem connected to the actuator, the stem projecting outwardly of the handle, the stem permitting the user to operate the actuator in either the first or second modes of operation permitted by the retainer; and an electrode forming a portion of the clamping surface of at least one of the jaws, the electrode capable of heating the portion of the patient's body that is grasped by the clamp to a desired temperature.

14. The surgical clamp assembly of claim 13, wherein the clamp includes:

a base having a bore therethrough, the first jaw being connected to the base;

a slot in the first jaw adjacent the connection with the base, the second jaw being disposed within the slot; and a hinge pin extending through the slot and the second jaw to support the second jaw for pivotal movement within the slot.

15. The surgical clamp assembly of claim 13, wherein the retainer includes:

a screw disposed within the bore, the screw having first and second ends;

a nut connected to the base, the screw passing through the nut, the connection between the nut and the screw being such that the screw can move toward the second jaw without rotating but the screw can move away from the second jaw only by being rotated;

a slot in the second jaw;

a link rotatably connected to the first end of the screw and connected to the second jaw by a pin passing through the link and the slot; and a drive connector connected to the second end of the screw, the actuator being connected to the connector in driving relationship.

16. The surgical clamp assembly of claim 13, further comprising an electrode on both jaws.

17. The surgical clamp assembly of claim 13, wherein the electrode is removable from the jaw to which it is attached.

18. The surgical clamp assembly of claim 13, wherein the electrode operates by a technique selected from the group consisting of resistance heating, radio frequency heating, and ultrasonic heating.

19. The surgical clamp assembly of claim 13, wherein the electrode is monopolar or bipolar.

20. The surgical clamp assembly of claim 13, wherein the electrode has a ceramic heating element made of barium titanate.

21. The surgical clamp assembly of claim 13, wherein the electrode has a surface that is heated substantially uniformly.

22. The surgical clamp assembly of claim 13, wherein the electrode has a surface that is heated non-uniformly.

\* \* \* \* \*